(12) United States Patent
Lee et al.

(10) Patent No.: US 11,439,334 B2
(45) Date of Patent: Sep. 13, 2022

(54) METHOD AND APPARATUS FOR CONTEXT-ADAPTIVE PERSONALIZED PSYCHOLOGICAL STATE SAMPLING FOR WEARABLE DEVICE

(71) Applicant: Korea Advanced Institute of Science and Technology, Daejeon (KR)

(72) Inventors: Uichin Lee, Daejeon (KR); Cheulyoung Park, Daejeon (KR); Soowon Kang, Daejeon (KR); Auk Kim, Daejeon (KR); Narae Cha, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 782 days.

(21) Appl. No.: 16/418,012

(22) Filed: May 21, 2019

(65) Prior Publication Data
US 2020/0330018 A1   Oct. 22, 2020

(30) Foreign Application Priority Data
Apr. 22, 2019 (KR) .......................... 10-2019-0046688

(51) Int. Cl.
*A61B 5/16* (2006.01)
*A61B 5/11* (2006.01)
(Continued)

(52) U.S. Cl.
CPC ............ *A61B 5/165* (2013.01); *A61B 5/1118* (2013.01); *A61B 5/16* (2013.01); *A61B 5/7267* (2013.01); *G06N 7/005* (2013.01); *G06N 20/00* (2019.01)

(58) Field of Classification Search
CPC ......... A61B 5/165; A61B 5/1118; A61B 5/16; A61B 5/7267; A61B 5/1123;
(Continued)

(56) References Cited

U.S. PATENT DOCUMENTS 11,284,834 B1 * 3/2022 Milbert ................. G16H 50/50
2017/0172493 A1 * 6/2017 Rahman ............ A61B 5/02055
(Continued)

FOREIGN PATENT DOCUMENTS

KR         20160097841 A        8/2016

OTHER PUBLICATIONS

English Abstract of KR20160097841A, Aug. 18, 2016.

*Primary Examiner* — Michael A Keller
(74) *Attorney, Agent, or Firm* — Cahn & Samuels, LLP

(57) ABSTRACT

Disclosed are a method and apparatus for sampling a context-adaptive personalized psychological state for a wearable device. The apparatus may include a sensor data collection unit configured to collect sensor data using a mobile and a wearable device, a physical activity classification unit configured to deduce a user's physical activities based on the collected sensor data, a sensor data unsupervised learning unit configured to group data based on extracted sensor data feature values for each deduced physical activity, a hierarchical psychological state classification unit configured to deduce a current psychological state as corresponding sensor data based on the data classified by the sensor data unsupervised learning unit, an information collection request determination unit configured to determine whether to request self-report information collection from a user based on at least one of the deduced current psychological state, collected label information, the sensor data or a degree of a user burden, and an information collection interface unit configured to receive self-report information from the user when the information collection request determination unit determines to collect the self-report information from the user.

8 Claims, 4 Drawing Sheets

(51) Int. Cl.
*G06N 7/00* (2006.01)
*G06N 20/00* (2019.01)
*A61B 5/00* (2006.01)

(58) Field of Classification Search
CPC .... A61B 5/7275; A61B 5/7264; G06N 7/005; G06N 20/00; G06N 3/0454; G06N 3/088; G16H 20/70; G16H 50/20; G16H 50/30; G16H 10/20; G16H 40/63
See application file for complete search history.

(56) References Cited

U.S. PATENT DOCUMENTS

2020/0151641 A1* 5/2020 Avegliano .............. G16Y 40/10
2022/0051773 A1* 2/2022 Appelbaum ........... G16H 10/40

* cited by examiner (a)

(b)

METHOD AND APPARATUS FOR CONTEXT-ADAPTIVE PERSONALIZED PSYCHOLOGICAL STATE SAMPLING FOR WEARABLE DEVICE

CROSS-REFERENCE TO RELATED APPLICATION

This application is based on and claims priority under 35 U.S.C. 119 to Korean Patent Application No. 10-2019-0046688, filed on 22 Apr. 2019, in the Korean Intellectual Property Office, the disclosures of which are herein incorporated by reference in their entireties.

BACKGROUND OF THE INVENTION

1. Technical Field

The present invention relates to a context-adaptive personalized experience sampling scheme capable of collecting robust and balanced label information and significantly reducing a user response burden by controlling a sampling method in real time based on a user's physical activity state and the features of collected data when the data of a user's psychological state, for example, an emotion state is collected.

2. Description of the Related Art

An experience sampling scheme is a scheme that extracts users' behaviors, thoughts, feelings, or emotion in daily life. For example, in the experience sampling scheme, a user's psychological state may be handled, and representatively a user's emotion and stress may be sampled. The user's emotion and stress state may be represented using various models.

Recently, various services monitoring a user's state in real time using a mobile and a wearable sensor to provide just-in-time feedback have been proposed. A smart device can automatically determine a user's location and activities. Furthermore, a bio signal, such as an electrocardiogram (ECG) indicative of a response of an autonomic nervous system, electrodermal activity (EDA), a skin temperature, electroencephalogram (EEG) or electromyograph (EMG), can be measured in real time using a wearable device. Representative application services include bio-feedback for a stress reduction and personalized psychological coaching according to an emotion state (e.g., depression). That is, a person's external information (e.g., location, activity, and user interaction) and internal information (e.g., a response of an autonomic nervous system) can be collected in real time using a mobile and a wearable device. Based on the gathered information, a user's psychological state can be classified in real time through machine learning.

In conventional machine learning, data collection that is used for model training is essential. When estimating variables related to user experiences including affective or psychological states, it is common to collect a training dataset where users self-report their experiences at a given time using an experience sampling method in daily life. The self-report means that the users select one of the predefined labels.

Such data collection method has some limits. First, a label distribution of sampled data may be biased. In general, a person's emotions, which are representative examples of the psychological state, vary over time but neutral emotions are likely to be more frequently observed. That is, emotions, such as anger or joy, are less frequently observed than neutral emotions. If random sampling is performed for collecting a user's self-report response, neutral emotions, which are observed relatively frequently, are more likely to be captured through experience sampling. Emotions other than the neutral emotions are less captured frequently, and thus the label imbalance phenomenon occurs.

The second is the noisy data problem of a mobile and a wearable sensor. A user's current body activity state may have a great influence on the quality of sensor data. A device for collecting a bio-signal may have a great change in quality depending on whether a user makes physical movements or the state in which the device has been worn. For example, it has been known that in the case of a sensor for measuring the heart rate, the variance of a measured value when a user moves is significantly greater than the variance when the user does not move, thereby resulting in very low accuracy.

Third, to secure a large number of labels, a user needs to be frequently inquired in daily life. It is likely that this frequent distractive inquiry negatively influences a user's daily life. The conventional experience sampling scheme causes a user burden because it could disturb a user's daily life by indiscreetly inquiring users without taking into consideration their context. If the context in which a user response burden is relatively low is found for experience sampling, a user's response burden can be significantly lowered, and thus, a user's response rate can also be improved.

SUMMARY OF THE INVENTION

An embodiment is to provide a method and apparatus capable of securing the quality of sensor data, solving a label imbalance problem, and significantly reducing a user response burden through a context-adaptive personalized experience sampling scheme for supplementing a collection method in real time based on collected data while collecting user experience data. Furthermore, an embodiment is to supplement an experience sampling method in real time in an information collection step in order to guarantee the quality of sensor data, reduce a user response burden and collect balanced user experience information when a user psychological state is sampled.

In an aspect, an apparatus for sampling a context-adaptive personalized psychological state for a wearable device includes a sensor data collection unit configured to collect sensor data using a mobile and a wearable device, a physical activity classification unit configured to deduce a user's physical activities based on the collected sensor data, a sensor data unsupervised learning unit configured to cluster data based on a plurality of sensor data features extracted for each deduced physical activity, a hierarchical psychological state classification unit configured to deduce a current psychological state as corresponding sensor data based on the data classified by the sensor data unsupervised learning unit, an information collection request determination unit configured to determine whether to request self-report information collection from a user based on at least one of the deduced current psychological state, collected label information, the sensor data or a degree of a user burden, and an information collection interface unit configured to receive self-report information from the user when the information collection request determination unit determines to collect the self-report information from the user.

The hierarchical psychological state classification unit is configured to perform hierarchical psychological state model training for assigning a label to each group trained by the sensor data unsupervised learning unit using self-reported labels collected from the user via the information collection interface unit and to perform classification on multiple labels when a plurality of labels is assigned to one group.

The hierarchical psychological state classification unit is configured to select a group closest to corresponding sensor data in order to deduce the current psychological state using the sensor data and to perform hierarchical psychological state model classification for deducing the current psychological state based on a distribution of labels assigned to the selected group.

The information collection request determination unit is configured to determine a value of a self-report information request to be presented to the user based on at least one of the deduced current psychological state, the collected label information, and the sensor data or the degree of a user burden. The determination of the value of the self-report information request includes at least one of the number of corresponding labels collected for a pre-defined time, a degree of model uncertainty improvement, the stability of label classification results using sensor data collected for a pre-defined time or a degree of a user burden related to self-reporting. The degree of a user burden can be measured at least one of the degree that current activities are disturbed, or a task workload of self-reporting.

The information collection interface unit is configured to present the information collection interface unit to the user so that the user self-reports his or her own psychological state according to a pre-defined self-report format and to request the user to perform labeling on a pre-defined past period in a current time or not to request self-report information collection for past data from the user when a measured change of a label is greater than a predetermined threshold.

In another aspect, a method of sampling a context-adaptive personalized psychological state for a wearable device includes the steps of collecting sensor data using a mobile and a wearable device through a sensor data collection unit, deducing a user's physical activities based on the collected sensor data through a physical activity classification unit, grouping data based on a plurality of sensor data features extracted from sensor data for each deduced physical activity through a sensor data unsupervised learning unit, deducing a current psychological state as corresponding sensor data based on the data through a hierarchical psychological state classification unit, determining whether to request information collection from the user based on at least one of the deduced current psychological state, collected label information, the sensor data or a degree of a user burden through an information collection request determination unit, and receiving self-report information from the user through the information collection interface unit when the information collection request determination unit determines to collect the self-report information from the user.

DETAILED DESCRIPTION

A psychological state monitoring scheme using the existing wearable device supports only a generalized model but does not support a personalized model. In other words, if a generic user's feedback regarding classification results is received, the detection accuracy of a psychological state (e.g., stress, emotion or depression) could be improved. For personalization, feedback needs to be received from a user, but to indiscreetly request feedback from the user may have a danger of significantly reducing user experiences due to user burdens. Accordingly, the present invention is a technology which may be applied to all fields including the mental health field, which monitors a psychological state using a mobile and a wearable device and provides personalized service to a user based on the psychological state. Embodiments of the present invention are described in detail below with reference to the accompanying drawings.

Figure 1:
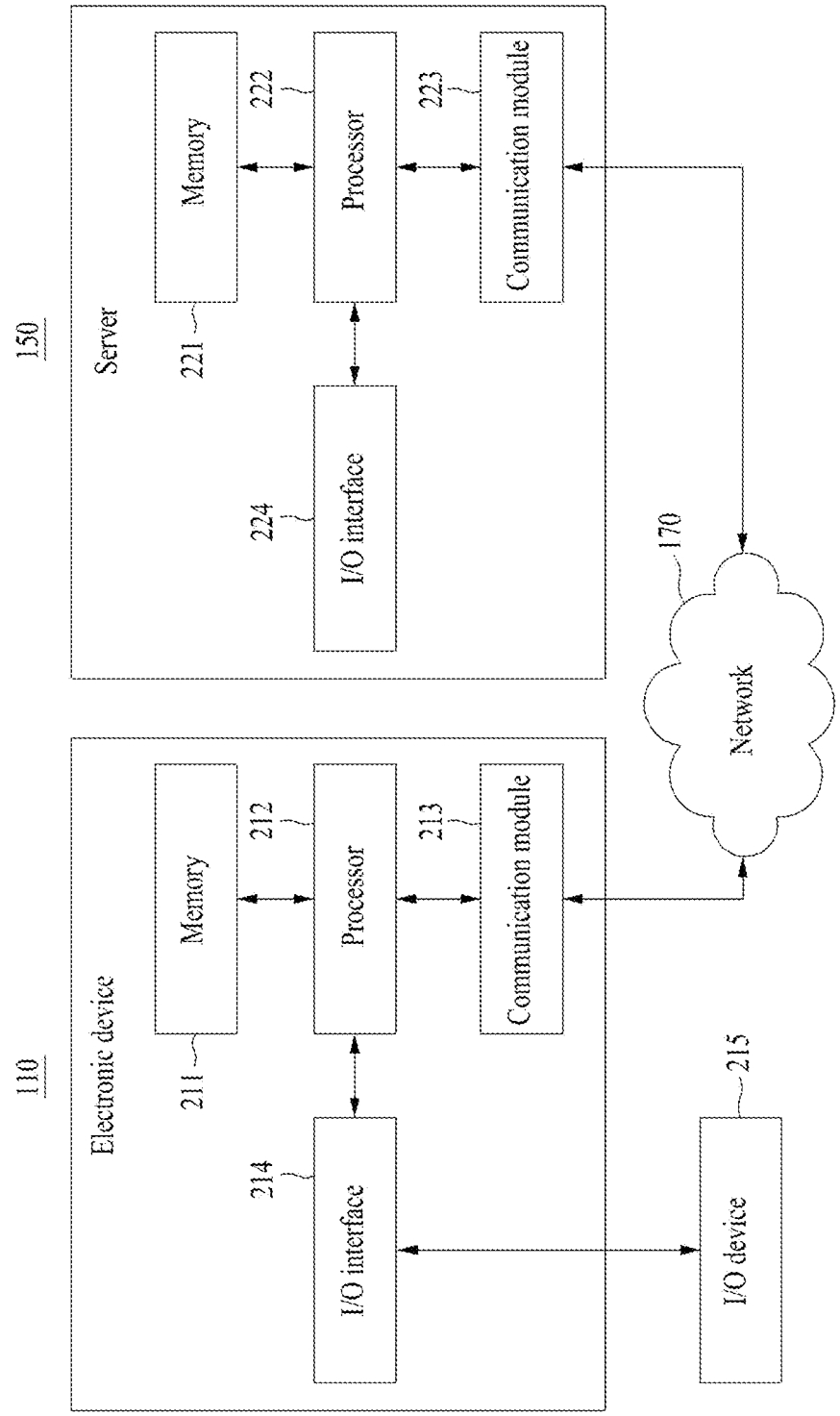
FIG. 1 is a block diagram for illustrating the internal configurations of a wearable device and a server according to an embodiment of the present invention.

FIG. 1 is a block diagram for illustrating the internal configurations of a wearable device and a server according to an embodiment of the present invention.

FIG. 1 is a block diagram for illustrating the internal configurations of the wearable device and the server. In FIG. 1, the internal configurations of the wearable device 110 and the server 120 are described as an example of a wearable device. Furthermore, other types of wearable devices or servers may have configurations identical with or similar to those of the wearable device 110 or the server 120.

The wearable device 110 and the server 120 may include memory 111 and 121, processors 112 and 122, communication modules 113 and 123, and input/output (I/O) interfaces 114 and 124, respectively. The memory 111, 121 is a non-temporary computer-readable recording medium and may include a permanent mass storage device, such as random access memory (RAM), read only memory (ROM), a disk drive, a solid state drive (SSD) or flash memory. The permanent mass storage device, such as ROM, SSD, flash memory or a disk drive, is a separate permanent storage device different from the memory 111, 121, and may be included in the wearable device 110 or the server 120. Furthermore, an operating system and at least one program code (e.g., code for a browser installed and driven on the wearable device 110 or an application installed in the wearable device 110 in order to provide a specific service) may be stored in the memory 111, 121. Such software elements may be loaded from a computer-readable recording medium separate from the memory 111, 121. Such a separate computer-readable recording medium may include a computer-readable recording medium, such as a floppy drive, a disk, a tape, a DVD/CD-ROM drive or a memory card. In other embodiments, such software elements may be loaded on the memory 111, 121 through the communication module 113, 123 other than a computer-readable recording medium. For example, at least one program may be loaded on the memory 111, 121 by developers or based on a computer program (e.g., the above-described application) installed by files provided over a network 170 by a file distribution system for distributing the installation file of an application.

The processor 112, 122 may be configured to process an instruction of a computer program by performing basic arithmetic, logic and I/O operation. The instruction may be provided to the processor 112, 122 by the memory 111, 121 or the communication module 113, 123. For example, the processor 112, 122 may be configured to execute an instruction received according to a program code stored in a recording device, such as the memory 111, 121.

The communication module 113, 123 may provide a function by which the wearable device 110 and the server 120 can communicate with each other over the network 170, and may provide a function by which the wearable device 110 and/or the server 120 communicates with a different wearable device or a different server. For example, a request generated by the processor 112 of the wearable device 110 based on a program code stored in a recording device, such as the memory 111, may be delivered to the server 120 over the network 170 under the control of the communication module 113. Inversely, a control signal or command, content, or a file provided under the control of the processor 122 of the server 120 may be received by the wearable device 110 through the communication module 113 of the wearable device 110 via the communication module 123 and the network 170. For example, a control signal or command, content, or a file of the server 120 received through the communication module 113 may be delivered to the processor 112 or the memory 111. Content or a file may be stored in a storage medium (e.g., the above-described permanent storage device) which may be further included in the wearable device 110.

The I/O interface 114 may be a means for an interface with an input and output device 115. For example, the input device may include a device, such as a keyboard, a mouse, a microphone or a camera, and the output device may include a device, such as a display, a speaker or a haptic feedback device. For another example, the I/O interface 114 may be means for an interface with a device in which functions for input and output have been integrated, such as a touch screen. The I/O device 115 may be integrated with the wearable device 110 as a single device.

Furthermore, the I/O interface 124 of the server 120 may be a means for an interface with a device (not shown) for input or output, which may be connected to the server 120 or may be included in the server 120. As a more detailed example, when the processor 112 of the wearable device 110 processes an instruction of a computer program loaded on the memory 111, a service screen or content configured using data provided by the server 120 or a wearable device may be displayed on a display through the I/O interface 114.

According to an embodiment of the present invention, the I/O interface 124 may include a sensor data collection unit 124a and an information collection interface 124b.

The sensor data collection unit 110 receives sensor data collected using a mobile and a wearable device. The range of collection of data includes at least one of pieces of bodily and contextual information, such as a user's activities, location/place, a smart device use history, ECG, EDA, a skin temperature, EEG, and EMG.

When the processor 122 determines to collect self-report information, such a determination may be provided to a user through the information collection interface 124b.

Furthermore, in other embodiments, the wearable device 110 and server 120 may include more elements than those of FIG. 1. However, most of conventional elements do not need to be clearly shown. For example, the wearable device 110 may be implemented to include at least some of the I/O device 115 or may further include other elements, such as a transceiver, a global positioning system (GPS) module, a camera, a variety of types of sensors, and a database. As a detailed example, if the wearable device 110 is a smartphone, in general, it may be implemented to include various elements, such as an acceleration sensor, a gyro sensor, a camera module, a variety of types of physical buttons, a button using a touch panel, I/O ports, and a vibrator for vibration which are included in the smartphone.

Figure 2:
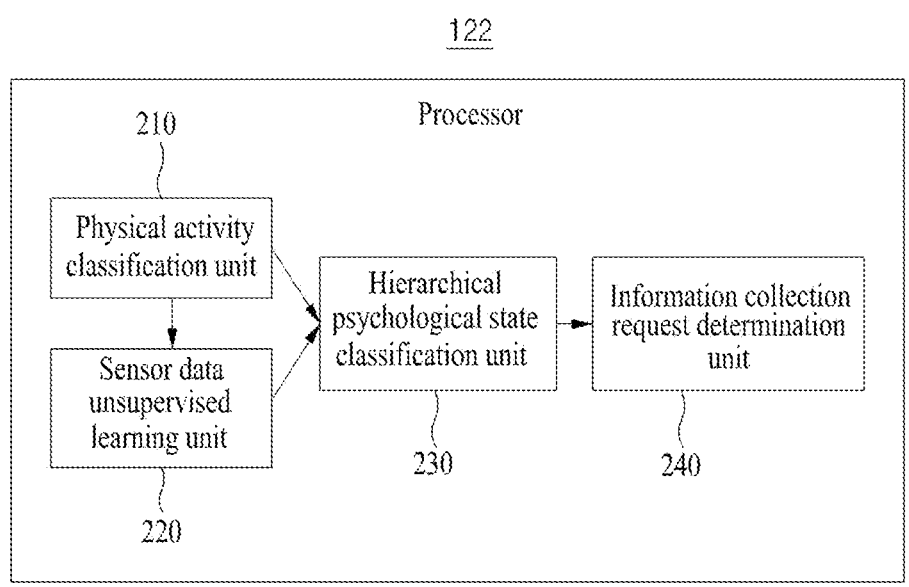
FIG. 2 is a block diagram showing an example of elements which may be included in the processor of the server according to an embodiment of the present invention.

FIG. 2 is a block diagram showing an example of elements which may be included in the processor of the server according to an embodiment of the present invention.

Sensor data may be collected through the wearable device 110 according to the present embodiment. For example, the wearable device 110 may be implemented in the form of a program that independently operates or may be configured in an in-app form of a specific application to operate on the specific application, and may provide sensor data to the server 120.

Figure 4:
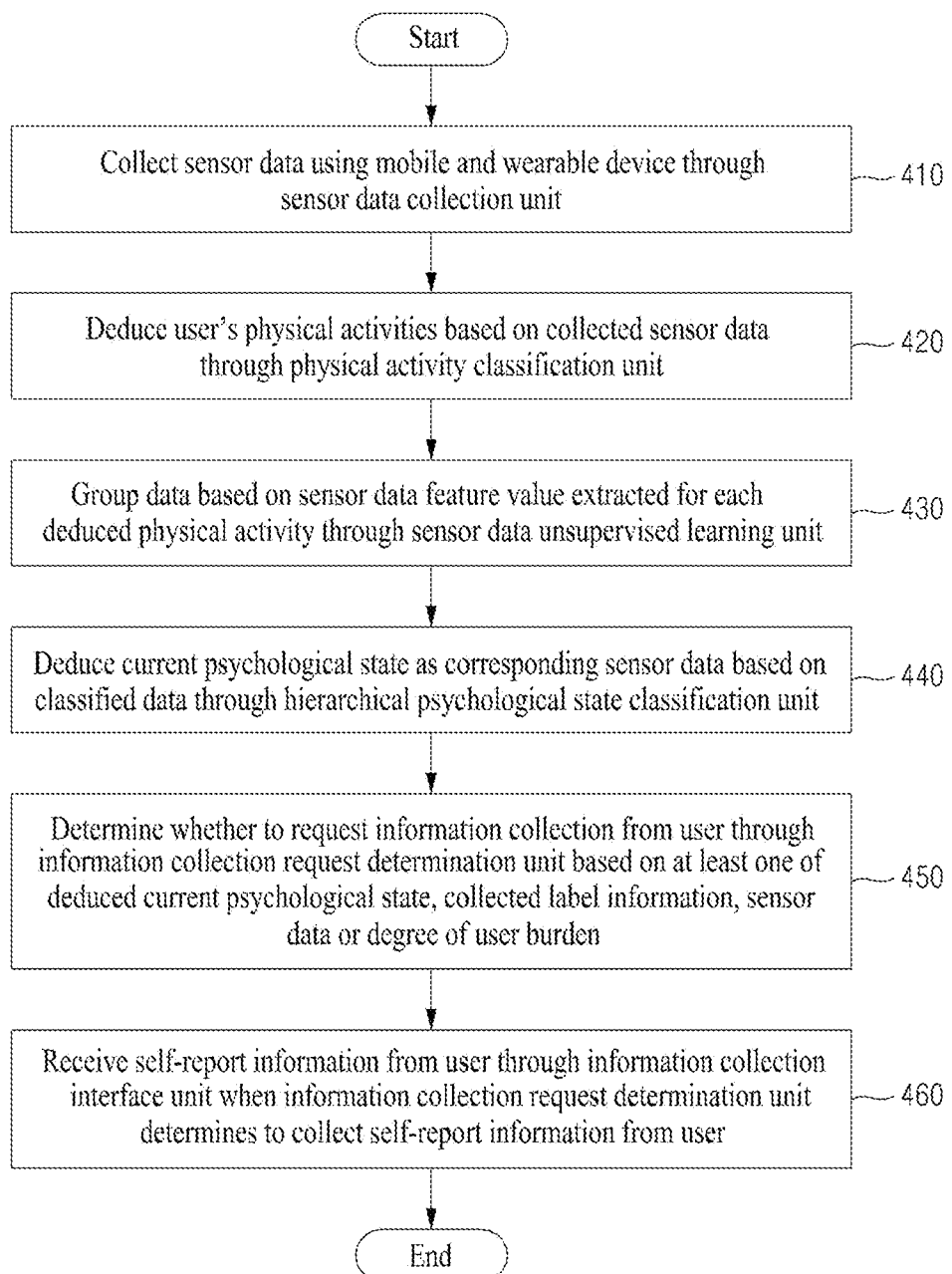
FIG. 4 is a flowchart for illustrating a method of context-adaptive personalized psychological state sampling for a wearable device according to an embodiment of the present invention.

The server 120 may perform a method of context-adaptive personalized psychological state sampling for a wearable device, shown in FIG. 4, using sensor data collected by the wearable device 110 based on an instruction provided by an application installed in the wearable device 110.

In order to perform the method of context-adaptive personalized sampling of a psychological state shown in FIG. 4, the processor 122 of the server 120 may include a physical activity classification unit 210, a sensor data unsupervised learning unit 220, a hierarchical psychological state classification unit 230, and an information collection request determination unit 240, as shown in FIG. 2. In some embodiments, the elements of the processor 122 may be optionally included in or excluded from the processor 122. Furthermore, in some embodiments, the elements of the processor 122 may be separated or merged for an expression of a function of the processor 122.

The processor 122 and the elements of the processor 122 may control the server 120 to perform steps 410 to 460 included in the method of sampling a context-adaptive personalized psychological state shown in FIG. 4. For example, the processor 122 and the elements of the processor 122 may be implemented to execute an instruction according to a code of an operating system and a code of at least one program included in the memory 121.

In this case, the elements of the processor 122 may be the expressions of different functions of the processor 122, which are performed by the processor 122 based on an instruction provided by a program code stored in the server 120 (e.g., instruction provided by an application driven in the server 120). For example, the physical activity classification unit 210 may be used as a functional expression of the processor 122 that controls the server 120 based on the above-described instruction so that the server 120 deduces a user's physical activities using collected sensor data.

The processor 122 may load an instruction from the memory 121 on which an instruction related to control of the server 120 has been loaded. In this case, the read instruction may include an instruction to be controlled by the processor 122 so that the instruction executes steps 410 to 460.

First, the sensor data collection unit 124a, that is, an element of the I/O interface 124 of FIG. 1, receives collected sensor data through mobile and a wearable device. The range of collection of data includes at least one of pieces of bodily and contextual information, such as a user's activities, a location/place, a smart device use history, ECG, EDA, a skin temperature, EEG, and EMG.

Thereafter, the physical activity classification unit 210, that is, an element of the processor 122, deduces a user's physical activities using the collected sensor data. The user's physical activities may include at least one of a stationary state, a walking state, or a running state. Various daily activities, for example, getting in the car, cleaning, and having a meal, may be additionally taken into consideration.

The sensor data unsupervised learning unit 220 groups the data based on a sensor data feature value extracted for each deduced physical activity and performs unsupervised learning specific to each physical activity using pre-defined major physical activity information. The unsupervised learning may be performed using the existing grouping scheme, for example, a k-means clustering model or a Gaussian mixture model (GMM). For unsupervised learning, a plurality of feature values need to be extracted from the sensor data. The feature values may be selectively extracted using the existing method chiefly used to extract bio-signal data. Alternatively, the feature values may be automatically extracted using a convolution neural network (CNN) or an auto-encoder.

The hierarchical psychological state classification unit 230 deduces a current psychological state from the sensor data based on the output of the sensor data unsupervised learning unit.

The hierarchical psychological state classification unit 230 classifies emotions based on various groups trained by the sensor data unsupervised learning unit 220.

First, a label may be assigned to each group, trained by the sensor data unsupervised learning unit using a label self-reported by a user through the information collection interface unit, through hierarchical psychological state model training. One or more labels may be assigned to one group. In such a case, multi-label classification is possible.

Figure 3:
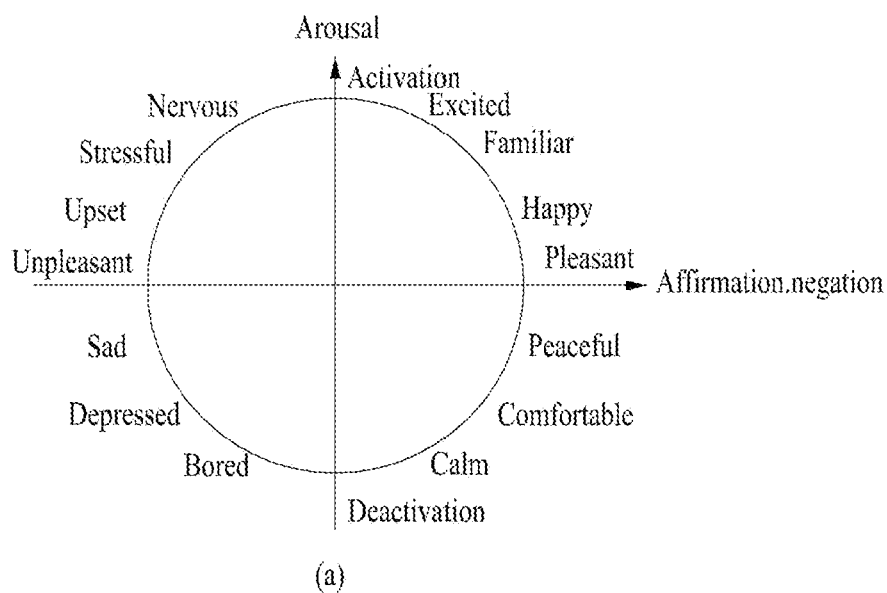
FIG. 3 is a diagram regarding Russell's emotion model for illustrating psychological states according to an embodiment of the present invention.
Figure 3:
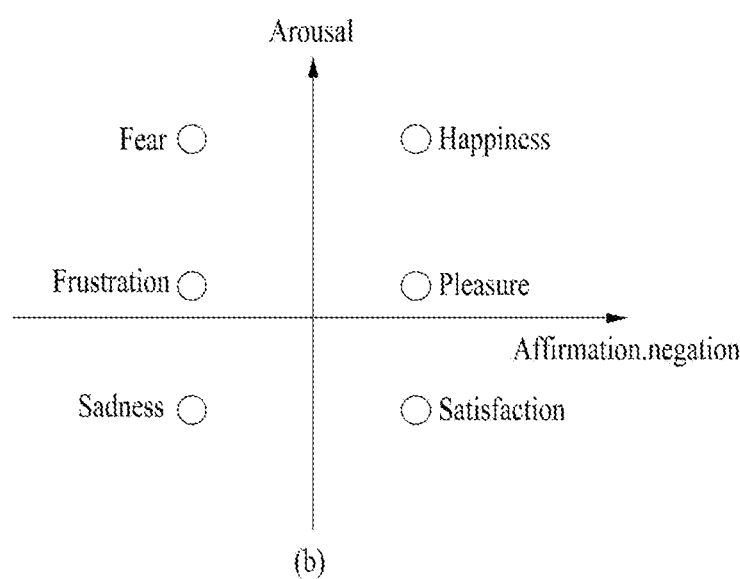

FIG. 3 is a diagram regarding Russell's emotion model for illustrating psychological states according to an embodiment of the present invention.

As shown in FIG. 3(*b*), Russell's emotion model is configured with two axes of valence and arousal. Various emotion states may be represented based on the two states as shown in FIG. 3(*a*).

In the case of emotion labeling using Russell's emotion model according to an embodiment of the present invention, emotion states may be labeled in a two-dimensional manner based on a degree of arousal and a degree of valence. Russell's emotion model defined in a two-dimensional manner may express common emotion adjectives (excited, familiar, happy, pleasant, peaceful, comfortable, calm, bored, depressed, sad, upset, stressful, nervous, etc).

In the case of emotion labeling using Ekman's emotion model according to another embodiment of the present invention, emotion states may include at least one of anger, fury, pleasure, sadness, surprise, or hatred.

A psychological state defined in the present invention may include at least one of emotions, stress, or depression. Russell's emotion model comprehensively includes such personal psychological states.

Referring back to FIG. 2, the hierarchical psychological state classification unit 230 deduces emotion states using current given sensor data through hierarchical psychological state model classification. In this case, the hierarchical psychological state classification unit 230 selects a group closest to corresponding sensor data and then deduces a current emotion state based on a distribution of labels assigned to a corresponding group.

The information collection request determination unit 240 determines whether to request self-information collection from a user based on at least one of the deduced current psychological state, collected label information, sensor data, or a degree of a user burden.

An expected label is extracted through the hierarchical psychological state classification unit based on currently collected sensor data. A value of self-report information request to be presented to a user is determined using extracted information. The determination of the value of the self-report information request includes at least one of the following: the number of corresponding labels collected for a pre-defined time, a degree of model uncertainty improvement, the stability of label classification results using sensor data collected for a pre-defined time, or a degree of a user burden on a self-reporting task.

A model for a degree of a user burden may be constructed through supervised learning, for example, multi-regression analysis using a user response and sensor data.

The stability of label classification results indicates a change in classification results for a pre-defined time and may be modeled using various statistical techniques.

In the case of a degree of model uncertainty improvement, uncertainty may be measured by performing supervised learning using collected label data.

The information collection interface unit 124*b*, that is, an element of the I/O interface 124 of FIG. 1, receives self-report information from a user if the information collection request determination unit 240 determines to collect self-report information from the user.

The information collection interface unit 124*b* enables a user to self-report his or her own psychological state in a pre-defined self-report format. For example, the psychological state may include a user's emotion state, a degree of stress, a degree that a user's daily activity is disturbed owing to a self-report request, etc. Furthermore, the user may be requested to perform labeling for a pre-defined past period at a current time. In other words, a label may be automatically generated using sensor data collected for a pre-defined past period through the hierarchical psychological state classification unit. The generated label is presented to the user so that the user may identify or modify the label. In order to reduce a user burden, a change of a label may be measured. When a change of a label is a threshold or more, a response request (identify or modify) for the past data may not be made because a danger of a recall error may be high.

FIG. 4 is a flowchart for illustrating a method of sampling a context-adaptive personalized psychological state for a wearable device according to an embodiment of the present invention.

The proposed method of sampling a context-adaptive personalized psychological state for a wearable device includes the step 410 of collecting sensor data using a mobile and a wearable device through the sensor data collection unit, the step 420 of deducing a user's physical activities based on the collected sensor data through the physical activity classification unit, the step 430 of grouping data based on a sensor data feature value extracted for each deduced physical activity through the sensor data unsupervised learning unit, the step 440 of deducing a current psychological state as corresponding sensor data based on the classified data through the hierarchical psychological state classification unit, the step 450 of determining whether to request information collection from the user through the information collection request determination unit based on at least one of the deduced current psychological state, collected label information, sensor data or a degree of a user burden, and the step 460 of receiving self-report information from the user through the information collection interface unit when the information collection request determination unit determines to collect the self-report information from the user.

At step 410, the sensor data collection unit collects sensor data using a mobile and a wearable device. The range of collection of data includes at least one of pieces of body information, such as a user's activities, a location/place, smart device use history, ECG, EDA, a skin temperature, EEG or EMG.

At step 420, a user's physical activities are deduced based on the collected sensor data through the physical activity classification unit. The user's physical activities may include at least one of a motionless state, a walking state or a running state. Various daily activities, for example, getting in the car, cleaning, and having a meal may be additionally taken into consideration.

At step 430, data is grouped based on a sensor data feature value extracted for each deduced physical activity through the sensor data unsupervised learning unit. Unsupervised learning specific to each physical activity is performed using pre-defined major physical activity information. The unsupervised learning may be performed using the existing grouping scheme, for example, a k-means clustering model or a Gaussian mixture model (GMM). For unsupervised learning, feature values need to be extracted from sensor data. The feature values may be selectively extracted using the existing method chiefly used to extract biosignal data. Alternatively, the feature values may be automatically extracted using a convolution neural network (CNN) or an auto-encoder.

At step 440, a current emotion is deduced as corresponding sensor data based on the classified data through the hierarchical psychological state classification unit.

The hierarchical psychological state classification unit classifies emotions based on various groups trained by the sensor data unsupervised learning unit.

First, a label may be assigned to each group, trained by the sensor data unsupervised learning unit, using a label self-reported by a user from the information collection interface unit through the hierarchical psychological state model training. One or more labels may be assigned to one group. In such a case, multi-label classification is possible. In the case of emotion labeling using Russell's emotion model according to an embodiment of the present invention, a label is possible in a two-dimensional manner based on a degree of arousal and a degree of affirmation/negation. In the case of emotion labeling using Ekman's emotion model according to another embodiment of the present invention, emotions may include at least one of anger, fury, pleasure, sadness, surprise or hatred.

After the hierarchical psychological state model training, an emotion state is deduced using current given sensor data through hierarchical psychological state model classification. In this case, a group closest to corresponding sensor data is selected. Thereafter, a current emotion state is deduced based on a distribution of labels assigned to a corresponding group.

At step 450, whether to request information collection from the user based on at least one of the deduced current psychological state, collected label information, the sensor data or a degree of a user burden is determined through the information collection request determination unit.

An expected label is extracted based on currently collected sensor data through the hierarchical psychological state classification unit. A value of self-report information request to be presented to the user is determined based on the extracted information. The determination of the value of the self-report information request includes at least one of the number of corresponding labels collected for a pre-defined time, a degree of model uncertainty improved, the stability of label classification results using sensor data collected for a pre-defined time or a degree of a user burden at a self-report time.

A model for a degree of a user burden may be constructed through supervised learning, for example, multi-regression analysis using a user response and sensor data.

The stability of label classification results shows a change in classification results during a pre-defined time and may be modeled using various technical statistic schemes.

In the case of a degree of model uncertainty improved, uncertainty may be measured by performing supervised learning using collected label data.

At step 460, when the information collection request determination unit determines to collect self-report information from the user, the self-report information is received from the user through the information collection interface unit.

The information collection interface unit enables a user to self-report his or her own psychological state in a pre-defined self-report format. For example, the psychological state may include a user's emotion state, a degree of stress, a degree that the activity of a self-report request is hindered, etc. Furthermore, the user may be requested to perform labeling for a pre-defined past period at a current time. In other words, a label may be automatically generated using sensor data collected for a preset past period through the hierarchical psychological state classification unit. The generated label is presented to the user so that the user may identify or modify the label. In order to reduce a user burden, a change of a label may be measured. When a change of a label is a threshold or more, a response request for the past data may not be made.

The existing wearable stress monitor does not receive personal feedback and does not advance a model. A model that may be extended to all common persons can be easily produced using physical activities, but it is very difficult to produce a general extensible model by monitoring psychological states including stress using a wearable device due to a deviation in a personal biosignal.

A wearable device for monitoring stress is described as an example of monitoring a psychological state including emotions. It is assumed that a generalized training model for determining stress is mounted on the wearable device for monitoring stress. However, the generalized training model has a good possibility that a deviation may be great in determination accuracy because personal features are not taken into consideration.

A user's activities are monitored in real time using a motion sensor, such as an accelerator mounted on a wearable device. Whether a user has a pre-defined limit of motion is determined using such real-time motion data. If there is a motion, whether the user walks or runs may be determined. Activity detection may be performed using a plurality of well-known machine learning methods.

When activities are extracted, a proposed system performs unsupervised learning based on sensor data received for each given physical activity. It is assumed that the wearable stress monitor includes at least one of biosignal sensor data, such as electrodermal activity (EDA), photo plethysmography (PPG) and skin temperature (SKT).

Features are extracted from corresponding bio signal sensor data. Skin conductance level (SCL) and skin conductance response (SCR) values may be extracted from EDA through signal processing. Features, such as an average conduction response and the number of responses, may be extracted based on the SCL and SCR values. An average, lowest or highest skin temperature may be extracted from an SKT. The amplitude mean and deviation of a blood flow rate may be extracted from the PPG as features. As an alternative to such a feature extraction method, after a signal can be wavelet-transformed, wavelet coefficients may be used as feature values. Alternatively, given input sensor data's dimension space may be reduced using an auto-encoder, and the reduced multi-dimension data could be used as feature values.

The sensor data unsupervised learning unit performs unsupervised learning using such an input feature value vector. For the unsupervised learning, a k-mean clustering model and a Gaussian mixture model (GMM) may be representatively taken into consideration. These two unsupervised learning models are representative machine learning models for clustering given input data into k groups. In the k-means clustering model, an input value is assigned to one of the k groups. In contrast, the GMM calculates probability values of a given data to belong to k groups. In the GMM, if the probability that a value of a given input vector will belong to each group is determined to be a preset threshold or more, the corresponding input vector is used to update the Gaussian model of each group. In the model update, a well-known method is to maximize a likelihood function. A different unsupervised learning model other than the k-means clustering model or the GMM can also be used for unsupervised learning.

In order to capture a change state of various sensor values for each given physical activity, a plurality of groups may be used. In order to capture various states of stress or various change states of emotions, for example, the number of groups may be set to 10.

An expected label may be extracted from given input sensor data through the hierarchical psychological state classification unit. The information collection request determination unit determines the value of a self-report information request to be presented to a user based on the extracted information.

The GMM may be trained using self-information collected by the system. In other words, a given label is assigned to a group detected in a model. For example, if the third group of the GMM has the highest probability value, a given label may be assigned to the third group. If input sensor data belongs to the third group, which label needs to be assigned to the input sensor data may be determined based on label information assigned to the third group. If a label belonging to the current third group consists of three samples of stress level 2, it may be determined as stress level 2. If the label is two samples of stress level 2 or three samples of stress level 3, the likelihood of stress level 2 may be deduced as 2/5 and that of stress level 3 may be deduced as 3/5 using the corresponding group as a probability value. Such a method may be considered to be a variation of k-nearest neighbor method. Since a group and a label are hierarchically mapped, such a method may be named a hierarchical psychological state classification method.

A value is determined using at least one of the number of corresponding labels collected for a pre-defined time, a degree of model uncertainty improvement, the stability of label classification results using sensor data collected for a pre-defined time, or a degree of a user burden at a self-report time.

If a user has been asked about a current stress level as a Likert-type scale between a point 1 and a point 5, which label will be questioned may be determined based on a distribution of labels for each corresponding point. For example, a stress level having the smallest label may be first questioned.

A degree of a user burden may be predicted by constructing a model through supervised learning, for example, multi-regression analysis using a user response and sensor data. The stability of label classification results indicates a change in classification results for a pre-defined time and may be modeled using various technical statistic schemes. A user may also answer how much to answer current self-report hinders an on-going work when the user reports a current stress level. For example, the user may answer how much to answer current self-report hinders current activities using the Likert-type scale between a point 1 and a point 5.

In a degree of model uncertainty improved, uncertainty may be measured by performing supervised learning using collected label data. The wearable stress monitor first detects stress using a stress detector in the system. The stress detector may be a model that is the results of the execution of supervised learning and trained using other persons' self-report information or maybe a model trained using self-report information. An improvement factor may be represented using a scale that directly or indirectly indicates the uncertainty of a trained model.

Sensor data is continuously generated in real time. Accordingly, continuous values may be monitored to determine a value using the sensor data. In order to conserve a limited resource (e.g., battery) of a wearable device, the system may perform duty cycling. That is, a corresponding value determination module may be configured to operate at a predetermined cycle.

When the information collection request determination unit determines to collect self-report information from a user, the information collection interface is presented to the user. The user may self-report its own stress state through a user interface according to a pre-defined self-report format. As described above, the user may give an answer using the 5-point Likert scale. Furthermore, the user may be questioned about how much a current self-report request disturbs current activities along with a corresponding self-report. When the value determination module does not continue to operate but operates in a duty cycle mode in a given cycle, the user may be inquired about his or her own past stress state corresponding collected sensor information. A hierarchical model classifier may automatically generate a label using sensor data collected during a pre-determined past period. The generated label may be presented to the user so the user may identify or modify the label. In order to reduce a user burden, a change of a label may be measured. When a change of the label is a threshold or more, a response request for the past data may not be made.

According to an embodiment of the present invention, an experience sampling method can be supplemented in real time in an information collection step in order to guarantee the quality of sensor data, reduce a user response burden, and collect balanced user experience information when a user psychological state is sampled.

Furthermore, the present invention has a good possibility that it can be used because the high quality of data necessary for the machine learning and artificial intelligence fields is collected, and thus prediction accuracy of a training model in a corresponding field can be significantly improved.

The present invention attempts to secure the quality of sensor data, solve a label imbalance problem, and significantly reduce a user response burden through the context-adaptive personalized experience sampling scheme for collecting user experience data and supplementing a collection method based on the collected data. It is expected that high quality of data necessary for the machine learning, artificial intelligence field can be collected using the method proposed by the present invention.

The aforementioned apparatus may be implemented in the form of a combination of hardware elements, software elements and/or hardware elements and software elements. For example, the apparatus and elements described in the embodiments may be implemented using one or more general-purpose computers or special-purpose computers, for example, a processor, a controller, an arithmetic logic unit (ALU), a digital signal processor, a microcomputer, a field programmable array (FPA), a programmable logic unit (PLU), a microprocessor or any other device capable of executing or responding to an instruction. The processing device may perform an operating system (OS) and one or more software applications executed on the OS. Furthermore, the processing device may access, store, manipulate, process and generate data in response to the execution of software. For the convenience of understanding, one processing device has been illustrated as being used, but a person having ordinary skill in the art may be aware that the processing device may include a plurality of processing elements and/or a plurality of types of processing elements. For example, the processing device may include a plurality of processors or a single processor and a single controller. Furthermore, other processing configurations, such as a parallel processor, are also possible.

The software may include a computer program, code, instruction or one or more combinations of them and may configure the processing device so that it operates as desired or may instruct the processing device independently or collectively. The software and/or data may be interpreted by the processing device or may be embodied in a machine, component, physical device, virtual equipment or computer storage medium or device of any type or a transmitted signal wave permanently or temporarily in order to provide instruction or data to the processing device. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure solely or in combination. The program instruction recorded on the recording medium may have been specially designed and configured for the embodiment or may be known to those skilled in computer software. The computer-readable recording medium includes a hardware device specially configured to store and execute the program instruction, for example, magnetic media such as a hard disk, a floppy disk, and a magnetic tape, optical media such as CD-ROM or a DVD, magneto-optical media such as a floptical disk, ROM, RAM, or flash memory. Examples of the program instruction may include both a machine-language code, such as code written by a compiler and a high-level language code executable by a computer using an interpreter.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and the equivalents of the claims belong to the scope of the claims.

In accordance with embodiments of the present invention, a data imbalance problem can be solved and a user response burden can be significantly reduced through the context-adaptive personalized experience sampling scheme for collecting user context data and supplementing and modifying an experience sampling method. Furthermore, the prediction accuracy of a training model in a corresponding field can be improved by collecting high quality of data necessary for the machine learning and artificial intelligence field.

What is claimed is:

1. An apparatus for context-adaptive personalized sampling of a psychological state for a wearable device, the apparatus comprising:
a sensor data collection unit configured to collect sensor data using a mobile and a wearable device;
a physical activity classification unit configured to deduce a user's physical activities based on the collected sensor data;
a sensor data unsupervised learning unit configured to group data based on sensor data feature values extracted for each deduced physical activity;
a hierarchical psychological state classification unit configured to deduce a current psychological state as corresponding sensor data based on the data classified by the sensor data unsupervised learning unit;
an information collection request determination unit configured to determine whether to request self-report information collection from a user based on at least one of the deduced current psychological state, collected label information, the sensor data or a degree of a user burden; and
an information collection interface unit configured to receive self-report information from the user when the information collection request determination unit determines to collect the self-report information from the user,
wherein the hierarchical psychological state classification unit is configured to:
perform hierarchical psychological state model training for assigning a label to each group trained by the sensor data unsupervised learning unit using a label self-reported by the user from the information collection interface unit, and
perform classification on multiple labels when a plurality of labels is assigned to one group.

2. The apparatus of claim 1, wherein:
the information collection request determination unit is configured to determine a value of a self-report information request to be presented to the user based on at least one of the deduced current psychological state, the collected label information, the sensor data, the degree of a user burden, and
the determination of the value of the self-report information request comprises at least one of a number of corresponding labels collected for a pre-defined time, a degree of model uncertainty improved, a stability of label classification results using sensor data collected for a pre-defined time or a degree of a user burden at a self-report time.

3. The apparatus of claim 1, wherein the information collection interface unit is configured to:

present the information collection interface unit to the user so that the user self-reports his or her own psychological state according to a pre-defined self-report format, and request the user to perform labeling on a pre-defined past period in current time or not to request self-report information collection for past data from the user when a measured change of a label is a predetermined threshold or more.

4. An apparatus for context-adaptive personalized sampling of a psychological state for a wearable device, the apparatus comprising:

a sensor data collection unit configured to collect sensor data using a mobile and a wearable device;

a physical activity classification unit configured to deduce a user's physical activities based on the collected sensor data;

a sensor data unsupervised learning unit configured to group data based on sensor data feature values extracted for each deduced physical activity;

a hierarchical psychological state classification unit configured to deduce a current psychological state as corresponding sensor data based on the data classified by the sensor data unsupervised learning unit;

an information collection request determination unit configured to determine whether request self-report information collection from a user based on at least one of the deduced current psychological state, collected label information, the sensor data or a degree of a user burden; and an information collection interface unit configured to receive self-report information from the user when the information collection request determination unit determines to collect the self-report information from the user, wherein the hierarchical psychological state classification unit is configured to:

select a group closest to corresponding sensor data in order to deduce the current psychological state using the sensor data, and perform hierarchical psychological state model classification for deducing the current psychological state based on a distribution of labels assigned to the selected group.

5. A method of sampling a context-adaptive personalized psychological state for a wearable device, the method comprising steps of:

collecting sensor data using a mobile and a wearable device through a sensor data collection unit;

deducing a user's physical activities based on the collected sensor data through a physical activity classification unit;

grouping data based on a sensor data feature value extracted for each deduced physical activity through a sensor data unsupervised learning unit;

deducing a current psychological state as corresponding sensor data based on the classified data through a hierarchical psychological state classification unit;

determining whether to request information collection from the user based on at least one of the deduced current psychological state, collected label information, the sensor data or a degree of a user burden through an information collection request determination unit; and receiving self-report information from the user through the information collection interface unit when the information collection request determination unit determines to collect the self-report information from the user, wherein the step of deducing the current psychological state as the corresponding sensor data based on the classified data through the hierarchical psychological state classification unit comprises:

performing hierarchical psychological state model training for assigning a label to each group trained by the sensor data unsupervised learning unit using a label self-reported by the user from the information collection interface unit, and performing classification on multiple labels when a plurality of labels is assigned to one group.

6. The method of claim 5, wherein:

the step of determining whether to request the information collection from the user based on at least one of the deduced current psychological state, the collected label information, the sensor data or the degree of a user burden through the information collection request determination unit comprises determining a value of a self-report information request to be presented to the user based on at least one of the deduced current psychological state, the collected label information, the sensor data, the degree of a user burden, and the determination of the value of the self-report information request comprises at least one of a number of corresponding labels collected for a pre-defined time, a degree of model uncertainty improved, a stability of label classification results using sensor data collected for a pre-defined time or a degree of a user burden at a self-report time.

7. The method of claim 5, wherein the step of receiving the self-report information from the user through the information collection interface unit when the information collection request determination unit determines to collect the self-report information from the user comprises:

presenting the information collection interface unit to the user so that the user self-reports his or her own psychological state according to a pre-defined self-report format, and requesting the user to perform labeling on a pre-defined past period in a current time or not requesting self-report information collection for past data from the user when a measured change of a label is a predetermined threshold or more.

8. A method of sampling a context-adaptive personalized psychological state for a wearable device, the method comprising steps of:

collecting sensor data using a mobile and a wearable device through a sensor data collection unit;

deducing a user's physical activities based on the collected sensor data through a physical activity classification unit;

grouping data based on a sensor data feature value extracted for each deduced physical activity through a sensor data unsupervised learning unit;

deducing a current psychological state as corresponding sensor data based on the classified data through a hierarchical psychological state classification unit;

determining whether to request information collection from the user based on at least one of the deduced current psychological state, collected label information, the sensor data or a degree of a user burden through an information collection request determination unit; and receiving self-report information from the user through the information collection interface unit when the information collection request determination unit determines to collect the self-report information from the user, wherein the step of deducing the current psychological state as the corresponding sensor data based on the classified data through the hierarchical psychological state classification unit comprises:

selecting a group closest to corresponding sensor data in order to deduce the current psychological state using the sensor data, and performing hierarchical psychological state model classification for deducing the current psychological state based on a distribution of labels assigned to the selected group.

* * * * *